US010339695B2

United States Patent
Petkov et al.

(10) Patent No.: US 10,339,695 B2
(45) Date of Patent: *Jul. 2, 2019

(54) CONTENT-BASED MEDICAL IMAGE RENDERING BASED ON MACHINE LEARNING

(71) Applicant: Siemens Healthcare GmbH, Erlangen (DE)

(72) Inventors: Kaloian Petkov, Lawrenceville, NJ (US); Shun Miao, Princeton, NJ (US); Daphne Yu, Yardley, PA (US); Bogdan Georgescu, Plainsboro, NJ (US); Klaus Engel, Nuremberg (DE); Tommaso Mansi, Plainsboro, NJ (US); Dorin Comaniciu, Princeton Junction, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 46 days.

This patent is subject to a terminal disclaimer.

(21) Appl. No.: 15/643,973

(22) Filed: Jul. 7, 2017

(65) Prior Publication Data

US 2017/0308656 A1 Oct. 26, 2017

Related U.S. Application Data

(63) Continuation of application No. 15/191,043, filed on Jun. 23, 2016, now Pat. No. 9,760,690.

(Continued)

(51) Int. Cl.
*G06T 15/50* (2011.01)
*G06T 15/06* (2011.01)
(Continued)

(52) U.S. Cl.
CPC ............ *G06T 15/06* (2013.01); *G06F 19/321* (2013.01); *G06K 9/6262* (2013.01);
(Continued)

(58) Field of Classification Search
None
See application file for complete search history.

(56) References Cited

U.S. PATENT DOCUMENTS

| 6,463,438 | B1 * | 10/2002 | Veltri | G06K 9/0014 |
| | | | | 706/15 |
| 6,690,371 | B1 * | 2/2004 | Okerlund | G06T 11/008 |
| | | | | 345/424 |

(Continued)

FOREIGN PATENT DOCUMENTS

| CN | 1509686 A | 7/2004 |
| CN | 103054602 A | 4/2013 |

(Continued)

OTHER PUBLICATIONS

Zhang, Jia-Wan, and Ji-Zhou Sun. "Adaptive transfer function design for volume renering by using a general regression neural network [renering read rendering]." Machine Learning and Cybernetics, 2003 International Conference on. vol. 4. IEEE, 2003.

(Continued)

*Primary Examiner* — Anh-Tuan V Nguyen (57) ABSTRACT

An artificial intelligence agent is machine trained and used to provide physically-based rendering settings. By using deep learning and/or other machine training, settings of multiple rendering parameters may be provided for consistent imaging even in physically-based rendering.

24 Claims, 2 Drawing Sheets

Related U.S. Application Data (60) Provisional application No. 62/306,407, filed on Mar. 10, 2016.

(51) Int. Cl.

| | | |
|---|---|---|
| *G06T 15/08* | (2011.01) | |
| *G06F 19/00* | (2018.01) | |
| *G06N 3/04* | (2006.01) | |
| *G06T 15/00* | (2011.01) | |
| *G16H 50/20* | (2018.01) | |
| *G06K 9/62* | (2006.01) | |
| *G06T 5/00* | (2006.01) | |

(52) U.S. Cl.
CPC ......... *G06K 9/6273* (2013.01); *G06N 3/0454* (2013.01); *G06T 5/00* (2013.01); *G06T 15/005* (2013.01); *G06T 15/08* (2013.01); *G06T 15/506* (2013.01); *G16H 50/20* (2018.01); *G06K 2209/05* (2013.01); *G06T 2210/41* (2013.01)

(56) References Cited

U.S. PATENT DOCUMENTS

| | | | |
|---|---|---|---|
| 6,999,549 B2 | 2/2006 | Sabol et al. | |
| 8,509,525 B1* | 8/2013 | Urbach | G06K 9/00449 345/440 |
| 8,520,906 B1* | 8/2013 | Moon | G06K 9/6263 382/118 |
| 8,711,144 B2 | 4/2014 | Johnson et al. | |
| 8,831,358 B1* | 9/2014 | Song | G06K 9/623 382/190 |
| 8,983,941 B1* | 3/2015 | Murphy-Chutorian | G06K 9/46 707/723 |
| 9,008,391 B1 | 4/2015 | Solanki et al. | |
| 9,014,485 B2 | 4/2015 | Moehrle | |
| 9,020,233 B2 | 4/2015 | Liu et al. | |
| 9,324,022 B2 | 4/2016 | Williams et al. | |
| 2003/0120651 A1* | 6/2003 | Bernstein | G06F 17/30569 |
| 2008/0118151 A1* | 5/2008 | Bouguet | G06F 17/30256 382/181 |
| 2008/0129732 A1 | 6/2008 | Johnson et al. | |
| 2012/0078062 A1* | 3/2012 | Bagchi | A61B 5/00 600/300 |
| 2014/0119672 A1 | 5/2014 | Ioffe et al. | |
| 2014/0277939 A1* | 9/2014 | Ren | G01C 21/3638 701/36 |
| 2015/0097842 A1* | 4/2015 | Kaasila | G06K 9/6215 345/471 |
| 2015/0100530 A1* | 4/2015 | Mnih | G06N 3/0454 706/25 |
| 2015/0161147 A1* | 6/2015 | Zhao | G06F 16/438 707/772 |
| 2016/0104057 A1* | 4/2016 | Shen | G06K 9/6256 382/159 |
| 2016/0189003 A1* | 6/2016 | Liu | G06K 9/6215 382/155 |
| 2016/0232658 A1* | 8/2016 | Syeda-Mahmood | G06K 9/00751 |
| 2016/0242740 A1* | 8/2016 | Day | A61B 8/5207 |
| 2016/0321523 A1* | 11/2016 | Sen | G06T 5/002 |
| 2017/0039297 A1* | 2/2017 | Koutrika | G06F 17/21 |
| 2017/0161607 A1* | 6/2017 | English | G06F 3/017 |
| 2017/0169620 A1* | 6/2017 | Bleiweiss | G06F 17/50 |

FOREIGN PATENT DOCUMENTS

| | | |
|---|---|---|
| CN | 103220974 A | 7/2013 |
| CN | 105389813 A | 3/2016 |

OTHER PUBLICATIONS

Xu Yan et al..: "Deep Learning of Feature Representation With Multiple Instance Learning For Medical Image Analysis"; 2014 International Conference on Acoustics, Speech and Signal Processing (ICASSP), IEEE, 2014, 5 pages.

Li Rongjian et al; "Deep Learning Based Imaging Data Completion for Improved Brain Disease Diagnosis"; Network and Parallel Computin; Lecture Notes in Computer Science; Springer international Publishing, Cham; pp. 305-312. [published 2014].

Partial Search Report dated Jun. 14, 2017 in corresponding International Application No. PCT/EP2017/055384.

Plis, Sergey M., Devon R. Hjelm, Ruslan Salakhutdinov, Elena A. Allen, Henry J. Bockholt, Jeffrey D. Long, Hans J. Johnson, Jane S. Paulsen, Jessica A. Turner, Vince D. Calhoun. "Deep learning for neuroimaging: a validation study." (2014), pp. 1-11.

Soundararajan, Krishna Prasad, and Thomas Schultz. "Learning Probabilistic Transfer Functions: A Comparative Study of Classifiers" Computer Graphics Forum. vol. 34. No. 3. 2015.

Zheng, Yefeng et al.: "3D Deep Learning for Efficient and Robust Landmark Detection in Volumetric Data", in: Int. Conf. on Medical Image Computing and Computer Assisted Interventions, 2015.

Lai M., Deep learning for medical image segmentation. arXiv preprint arXiv:1505.02000. May 8, 2015, pp. 1-23.

Chinese Office Action dated Mar. 25, 2019 in corresponding Chinese Patent Application No. 201780016345.8.

Wenhua Wang; "Real-Time Interactive Visualization in Medical"; 2010; pp. 1-72.

* cited by examiner

CONTENT-BASED MEDICAL IMAGE RENDERING BASED ON MACHINE LEARNING

RELATED APPLICATIONS

The present patent document is a continuation of U.S. patent application Ser. No. 15/191,043, filed Jun. 23, 2016, which claims the benefit of the filing date under 35 U.S.C. § 119(e) of Provisional U.S. Patent Application Ser. No. 62/306,407, filed Mar. 10, 2016, which are hereby incorporated by reference.

BACKGROUND

The present embodiments relate to medical imaging of three-dimensional (3D) scans. Data representing a volume is rendered for visualization. Due to the many different scan settings and patient variability, renderings for different patients or at different times appear different.

In an effort to reduce variability, most existing medical rendering provides a set of static visualization presets for specific workflows or diagnostic contexts. Even with static presets, the rendering may require manual adjustment and may not provide consistent rendered results. Semi-automatic machine learning approaches have been used to provide transfer function design in traditional volume rendering (e.g., projection or alpha blending), but may still not sufficiently reduce variability.

Variability is particularly troublesome for physically-based volume rendering, which relies on the physical simulation of light propagation (e.g., unbiased path tracing). Physically-based visualization techniques produce global illumination effects in computer-generated graphics that mimic the real-world interaction of light with various 3D objects or tissues. This results in physically plausible images that are often easier for the human brain to interpret when compared to the more analytical images from traditional rendering. For example, subtle ambient occlusions, shadows, and color bleeding provide important depth cues for the spatial understanding of 3D relationships between structures in a single 2D image, whereas simpler visualization techniques may require additional interaction with the viewing parameters (e.g., moving the virtual camera around the 3D data) to obtain the same spatial information from the image parallax.

These physically-based visualization techniques are more sensitive to changes in the classification or the interpretation of the underlying medical data. As a result, small changes to the rendering parameters may have a more pronounced impact on the perception and interpretation of 3D structures in the final image as compared to the traditional volume rendering techniques based on compositing of classified voxels along viewing rays. Obtaining very high quality reproducible images with diagnostic significance is then partially at the user's discretion. While existing techniques for providing visualization presets can help, the workflow is not fully automated and the resulting rendered images may not have consistent quantitative properties (color, hue, reflectance, etc.) across datasets.

BRIEF SUMMARY

By way of introduction, the preferred embodiments described below include methods, systems, instructions, and computer readable media for machine training an artificial intelligence and use of that artificial intelligence to provide rendering settings. By using deep learning and/or other machine training, settings of multiple rendering parameters may be provided for consistent imaging or visualization even in physically-based rendering.

In a first aspect, a method is provided for content-based rendering based on machine learning in a rendering system. A medical dataset representing a three-dimensional region of a patient is loaded from memory. A machine applies the medical dataset to a machine-learnt non-linear model. The machine-learned model is trained with deep learning to extract features from the medical dataset and trained to output values for two or more physically-based rendering parameters based on input of the medical dataset. At least one of the two or more physically-based rendering parameters are controls for consistent data handling, lighting design, viewing design, material propriety, or internal renderer property. A physically-based renderer renders a photorealistic image of the three-dimensional region of the patient using the output values resulting from the applying. The photorealistic image is transmitted.

In a second aspect, a method is provided for machine training for content-based rendering in a machine training system. First volume data of a volume of a patient, a first image of the volume, and first values of path tracing rendering parameters are input to training of an artificial intelligence. A machine trains the artificial intelligence to output second values of the path tracing rendering parameters for a second volume data where the second values provide a second rendered image of the second volume modeled on the first image. The trained artificial intelligence is stored.

In a third aspect, a system is provided for content-based rendering based on machine learning. A medical scanner is configured to scan a patient. A machine is configured to output settings for rendering parameters by application of data from the scan to a machine-learnt model. The rendering parameters include windowing, transfer function, and lighting, and the settings are learned to provide a first image from the data similar to one or more second images for a same diagnostic context. A graphics processing unit is configured to render the first image using the settings.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Content-based photorealistic rendering of medical images is based on machine learning. To produce consistent rendered images from 3D medical scans, particularly when using physically-based rendering techniques, the machine learnt non-linear model determines rendering settings based on the content of the 3D medical scan. Due to the variability between scan parameters, data contrast, noise, and/or the large number of rendering parameters, producing rendered images that allow for consistent visual interpretation has been a long standing challenge, which has prevented wider adoption 3D images for definitive decision support.

In one embodiment, deep learning generates the settings for the rendering parameters for the photorealistic rendering components, establishing a consistent visualization design. This design may be applied to new 3D image data in order to provide reliable visual interpretation within the diagnostic workflow. Image features, and optionally, available non-image data are mapped to sets of rendering parameters that produce optimal images, where the relationship between the two is highly non-linear in the general case. By targeting the entire or multiple parts of the rendering pipeline, a scalable solution leverages machine learning and supports consistent photorealistic rendering.

Consistent visual interpretation for 3D images may potentially simplify diagnostic workflow and may promote the clinical use of 3D data for decision support. Consistent photorealistic rendered images may be provided in new platforms and workflows, such as fully automated reporting and cloud-based rendering services. Consistent visualization design as a machine learning problem may be applied 1) to optimize rendering preset designs tailored to a large variety of data types in a unified and scalable way, 2) to adapt rendering parameters to produce target consistent results based on the provided input, 3) to adapt rendering parameters to specific individual preferences, 4) to transfer expert trained results to non-expert users, 5) to increase the conspicuity of visual features in the rendered images (e.g., pathologies in medical images) and 6) to provide automatic rendering presets for specific workflows. A scalable framework is provided for fully automated image generation in the clinical workflow.

Figure 1:
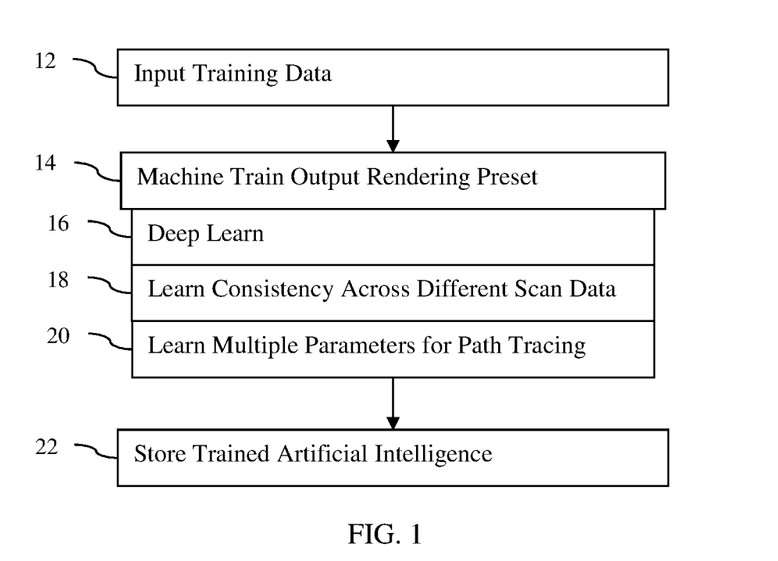
FIG. 1 is a flow chart diagram of one embodiment of a method for machine training for content-based rendering.

FIG. 1 shows one embodiment of a method for machine training for content-based rendering in a machine training system. Optimal rendering parameters may be obtained via training an artificial intelligence system. The input of the artificial intelligence system may include, but is not limited to, the 3D scan data to be rendered, images rendered from the 3D scan data, information on the patient, and/or information on the diagnostic purpose. Using many examples, the machine training learns to provide rendering settings for photorealistic rendering based on input data for a specific patient. The output of the trained artificial intelligence system is the optimal set of settings for the rendering parameters.

The method of FIG. 1 is implemented by a processor and a graphics processing unit in a server, computer, or other machine. In one embodiment, the system of FIG. 3 implements the method of FIG. 1, with or without the medical imager 56 and/or display 54. For example, data is input by loading from a memory, a processor performs the training based on the data, and the memory stores the learnt artificial intelligence. As another example, the medical scanner and/or memory input the data to a server, which performs the training and outputs to a memory.

The acts are performed in the order shown (top to bottom) or another order. For some forms of learning, results may be fed back as input in a repetition of the acts.

Additional, different, or fewer acts may be provided. For example, act 22 is not provided, such as where the trained artificial intelligence is used rather than stored for later use.

In act 12, training data is input. The training data is gathered from one or more memories, sensors, and/or scanners. The gathered data may be stored and/or transmitted to a buffer, memory, cache, processor, or other device for training. This gathered training data is input to the machine learning algorithm.

Many samples of the same type of data are input. To learn statistical or other relationships that may be sufficiently complex that a human cannot perceive the relationships in a same level, tens, hundreds, or thousands of samples are provided.

Any data may be used. Since the artificial intelligence is to be trained to provide settings for rendering parameters, scan data is provided. For each sample, the scan data represents a patient. A two-dimensional (2D), 3D, 2D+time sequence, 3D+time sequence, and/or other image or scan data may be used.

Other information than scan data may be provided for each sample. Patient non-image data may be input to the training. Higher dimensional data includes but is not limited to patient information such as a) natural language medical documents or information extracted therefrom of previous diagnosis and/or clinical procedures; b) previous medical test results; c) previously processed medical images and measurements; d) computational modeling results; e) parametric image information derived from medical image analysis algorithms (e.g. cardiac strain map or elasticity); and/or f) other information (e.g., scanner settings).

For training, the goal or ground truth information is input. The artificial intelligence system is trained with labeled data (e.g., pairs of input and corresponding desired output (e.g., rendering parameters, optimal rendered images, and/or photographs/movies of the real object)). Based on the provided data, the artificial intelligence system is trained to produce the desired output from any input. The ground truth is provided by desired settings of the rendering parameters for each scan dataset. The values of the path tracing rendering parameters for desired results of each sample are input to the training. Alternatively or additionally, the ground truth is provided as a desired rendered image for each scan dataset. A rendered image for each scan dataset is provided. In other embodiments, an image with desired visualization is provided for multiple datasets. Using a renderer, the machine training may learn the settings that produce similar visualization.

The input samples may provide both negative and positive training samples. For example, scan datasets and settings providing desired and undesired images are input. The training learns to distinguish the desired settings from both good and bad settings.

In one embodiment, additional samples are created by perturbing the path tracing rendering parameters of an input sample. The perturbing creates a collection of sets of the path tracing rendering parameters for each scan data set. The artificial intelligence system is applied on the input scan dataset to generate rendering parameters, which are then perturbed to generate a pool of rendering parameters. Rendering is then performed using the sets of rendering parameters in the pool to produce a pool of corresponding images. Human users or other operators then visually examine the produced images and select the satisfying images. The rendering parameters for the selected images are then used as desired output and/or a sub-set as positive ground-truth.

The rendering parameters for the unselected sub-set of images are not used or are used as negative ground-truth.

In another approach to gather samples for input, a web-based or network-based service is provided. A website or network portal allows a user to upload the input data (i.e., image and additional information). The server or other processor then runs the artificial intelligence system and/or perturbs possible rendering settings to renderer a pool of images. The service then provides the generated images to the user and asks the user to select the satisfying images. The rendering parameters corresponding to the user selected images are then stored as the desired output for the input (i.e., ground truth). By providing such a service, additional samples for training may be gathered over time.

The input may be repeated. The training of the artificial intelligence system is performed periodically or multiple different times. After additional samples are collected (e.g., through the web-based service), the training is repeated using the additional samples with or without previous samples used for earlier iterations of the training.

In act 14, the artificial intelligence or intelligences are machine trained. The collected samples, including ground truth, are used to train. A machine, such as a processor, computer, server, or other device learns from the samples. Using machine-learning, complex statistical relationships between large numbers (e.g., tens, hundreds, thousands, or more) of input variables to any number of output variables are extracted from the large number of samples.

The training is for imaging in any context. One model may be learned for any number of imaging situations. Alternatively, different models are trained for different situations. The different situations may include different scan modalities (e.g., different model for computed tomography, magnetic resonance, ultrasound, positron emission tomography, and single photon emission computed tomography). The different situations may include different types of tissue of interest (e.g., liver versus kidney), different diagnostic purpose or workflow (e.g., cancerous lesion versus bone calcification), and/or different users (e.g., different operators may have different preferences for visualization).

Any now known or later developed machine learning may be used. Regression, classification, and/or reinforcement learning are used. Regression training learns a range or continuous output by minimization of a metric. Classification learns disparate outputs. Reinforcement learning learns through a sequence of actions with feedback. Neural network, Bayes network, or support vector machine training may be used. Hierarchal or other approaches may be used. Supervised or semi-supervised machine learning may be used.

To train, features are extracted from the input data. Haar wavelet, steerable, or other features may be extracted from the scan dataset or images. Measures or other information may be extracted from non-image data. Alternatively, the input data itself (e.g., scalar values of the scan dataset) is used.

In an alternative represented in act 16, the machine learns features as part of the training. For example, deep learning (e.g., deep structured learning, hierarchical learning, or deep machine learning) models high-level abstractions in data by using multiple processing layers with structures composed of multiple non-linear transformations, where the input data features are not engineered explicitly. A deep neural network processes the input via multiple layers of feature extraction to produce features used to derive outputs of settings for rendering. The deep learning provides the features used by other machine training to learn to output the rendering settings. Other deep learnt, sparse auto-encoding models may be trained and applied. The machine training is unsupervised in learning the features to use and how to classify given an input sample (i.e., feature vector).

Using deep learning, the input features required for the machine learning are not engineered by the user explicitly, as in shallow learning algorithms. This is especially useful with render settings, which may not have an explicit natural relationship with the input data. Deep learning figures out the data features that end up providing a good classifier or model. Deep learning is known to be effective in extracting high level abstractions (features) from low level input data (e.g., raw images) that is suitable for the trained task, so may be more convenient than and superior to hand-crafted features for identifying features for render settings. In addition, learning-based automatically rendering setting selection is a less studied problem, with no hand-craft feature specifically designed for this problem. Standard hand-craft features, like HAAR feature or SIFT feature, designed for other general computer vision tasks may not be suitable for rendering setting.

In act 18, the machine trains to output rendering settings to provide consistent imaging. To reduce variability, the training learns to provide rendering settings that result in a rendered image with similar or same visualization despite differences in the content of the data. The path tracing or other physically-based rendering settings so that the rendered image for a given input scan dataset looks and feels similar to an ideal are learned. The machine learns to output renderer settings to model the resulting rendered image for a given scan dataset on a desired image. The learned sets of parameters establish a visualization design that may be reused when new data is introduced to the system in order to provide consistent rendered images. In this way, the machine may learn renderer settings to provide rendering to a standard. Rather than render with the same preset values for a given context, the values are based on a given input dataset. In various embodiments of the system, consistency refers to consistent data handling, consistent viewing, and/or consistent visual styles, which may be utilized both in automated and interactive clinical workflows.

The ground truth provides consistency. Where the ground truth uses similar or consistent images and/or settings that result in similar or consistent images despite variance in the scan datasets, the training learns to output settings providing the consistency. The notion of optimal rendering parameters and optimal output images relates to using objective quality measurements, subjective quality measurements, clinical significance ratings, and/or other indicators of consistency.

In one embodiment, the consistency is learned using a measured or calculated metric. The training uses a metric of similarity. Any metric of similarity may be used. Example computed metrics may be visual perception metrics based on visual systems, comparative differences, perceptual hash, mutual information, correlation, computed feature signals, or simple error metrics. The metrics may be automatically computed or provided by the users. The metric is used as an indicator of strength of importance of a given training sample.

Alternatively or additionally, one or more metrics are used in reinforcement learning. For example, deep reinforcement learning uses a similarity of the rendered image from a sample to a reference image. The similarity is used as a reinforcement. The output image rendered from a given set of rendering settings for a sample of scan data and the associated quality metrics (i.e., similarity) are fed-back into the learning system for additional refinement of the learned parameters (e.g., in deep supervised and/or reinforcement learning). A metric measuring the similarity of one rendered image to one or a group of rendered images with the desired quality is calculated, and used as the "reward" to train the artificial intelligent agent using the deep reinforcement learning technique.

Other quality metrics than similarity may be used. The choice of metric to use may depend on the types of features relevant to a specific clinical data domain. Depending on the diagnosis of interest or medical workflow, different pathologies may be of interest. Different rendering settings increase the conspicuity of different pathologies. The quality metric in the reinforcement learning is used to learn to provide the optimal rendering parameters for increasing the conspicuity of the pathology of interest.

In one embodiment, the artificial intelligent agent is a deep neural network that takes in the output of the reinforcement agent as its input, and outputs one quality or similarity metric (referred to as "action-value") for each possible action (e.g., set of rendering settings), indicating the effect of taking these actions (i.e., higher values are associated with actions that can improve the rendering quality). The agent also analyzes the action-values, and selects one action to perform. The set of rendering parameters providing the highest implementable quality rendering are selected as the output.

In another embodiment, a probability distribution of different values of the metric (i.e., different similarities) is used for the selection. The selected action is the action with highest action-value or randomly selected from the actions with a probability distribution assigned based on the rank of action-values. In a typical scenario, actions with higher action-values are assigned higher probability, but any assignment may be used.

In other or additional reinforcement learning, the training is modeled after steps taken by an expert or other user to achieve the desired visualization for the training data. The user's sequence of adjustments to provide the desired rendering from the scan dataset is monitored (e.g., select transfer function T1, then window function W1, then select a different transfer function T2, then select a material reflectance MR1, . . . ). The learning uses metrics for each stage or step to learn the settings used for each. The actions of the expert are extrapolated to different training datasets or included for each training dataset. The training learns to provide final rendering settings based on the monitored sequence.

Rather than using a rendered image or multiple rendered images as the ground truth and/or for calculating similarity, a photograph or video of the imaged tissue, imaged object, or other real-world references is used. The physically-based rendering provides photorealistic images. By comparing or training to real photos or video, the training learns to provide rendering settings modeled after real images. The desired output is labeled using actual optical images so that the rendering parameters result in a matching look and/or feel. Other modes of images may be used for the ground truth or reinforcement metric, so that the training learns to output rendering settings modeled after the different modality (e.g., render CT data to match the look of rendered MR data).

In act 20, one model is trained to output settings for multiple rendering parameters. In other embodiments, a hierarchy or other grouping of models are trained to output the settings for multiple rendering parameters. Using the training data and ground truth, the machine is trained to output settings of rendering parameters. By outputting settings for two or more rendering parameters for a given scan dataset, less manual setting of parameters is needed. In path tracing or other physically-based rendering, the amount of processing and time required to provide the photorealistic imaging may cause delays. Compounding such delays with user adjustment, it may be overly time consuming to provide a desired rendering manually. By using machine learning to provide the initial settings for multiple parameters, the machine trained model contributes to less delay in achieving the desired rendered image.

The model may be trained to output any number and/or type of rendering parameters. For example, one or more data consistency parameters are to be output. Data consistency parameters include windowing, scaling, level compression, data normalization, or others. As another example, one or more transfer function design parameters are to be output. Transfer function design parameters include classification look-up tables, multi-dimensional transfer functions, tissue-specific transfer functions, or other transfer functions. In another example, one or more lighting design parameters are to be output. Lighting design parameters include type of virtual lights, position of the virtual light sources, orientation of the virtual light sources, image-based lighting sources, or others. In yet another example, one or more viewing design parameters are to be output. Viewing design parameters include type of camera, position of the camera, orientation of the camera, intrinsic parameters for viewing, or others. In other examples, one or more use-case specific parameters are to be output. Use-case specific parameters are settings specific to a given use, such as a particular camera position for a given type of medical report or use of two cameras for stereoscopic viewing.

The parameters may be specific to physically-based rendering, such as internal render properties. The setting for any parameter for path tracing, unbiased path tracing, Monte Carlo rendering, global illumination, or other simulations of light propagation may be learned. For example, a global albedo, or surface reflectance coefficient, may be learned for the volume data, which describes the relative importance of light scattering versus light absorption. Settings for any parameters for material property controlling the interaction with light may be learned. For example, the transparency, reflectivity, surface roughness, and/or other properties may be modeled in the physically-based rendering, so included as rendering parameters. Albedo may also be learned as a per-material property for the different tissue classes in the volume data. Since the effect of various settings of material type or light interaction may not be instinctive to a user, training the model with machine learning to provide the initial settings may assist the user.

All or a sub-set of the rendering parameters are to be output by the machine-learnt model. For example, the model is trained to output any number of data consistency, transfer function, lighting, and viewing parameters. For fully automatic, the model is trained to provide settings for all of the rendering parameters. For interactive or other semi-automatic operation, the model is trained to provide settings for some but not all of the rendering parameters. For example, all of the rendering parameters are output except for the view design parameters, which are under the control of the user. The viewing camera parameters are under the control of the user, so the machine learning is for settings of other parameters. The user controls the view design parameters independently.

The model is trained to output settings for multiple parameters regardless of the user-controlled parameters. Alternatively, the user-selected parameters are an input to the classification so that the output settings account for the user-selected settings. The model learns to output rendering parameter settings based, in part, on settings for one or more parameters under the control of the user. The artificial intelligence is trained to output the values for the rendering parameters based on user selected viewing camera parameters. Subsets of the rendering parameters are used as additional inputs in the training phase of the machine learning algorithm. In that case, the machine learning algorithm output is an optimized subset of the rendering parameters. The user input settings may be optimized or not while the other settings are optimized by the model. In an interactive viewing application, the input to the training is a higher dimension vector including the input scan dataset and reference viewing parameters.

In another embodiment, the artificial intelligence is trained to account for different ambient conditions in the real-world viewing environment of the user. The settings for "ambient-varying" rendering of a volume are learned. The training data includes different ambient light conditions and measures of the ambient light using light probes. The model is trained to account for ambient luminosity of the room. The luminosity is sent to the trained model, which adapts the rendering parameters automatically to provide the same content-based realistic rendering.

The training may be repeated. As the machine-trained model is used, the user may adjust some of the output settings. This adjustment, the setting, and/or image resulting from the adjustment are added to the training data. The machine learning model is refined by repeating the learning with the addition feedback as samples from which to learn. The manually adjusted settings of the parameters define personalized visualization designs. Other sources of further training data may be used.

The repetition of the training may be performed separately for different users, physicians, medical groups, hospitals, or other grouping. Personalized training is used so that consistent images for a relevant group are provided. In other embodiments, the repetition is provided for all users.

In act 22, the trained artificial intelligence is stored. The result of the training is a matrix. The matrix represents the learned knowledge through machine training. The matrix includes an input vector and outputs for the settings of the rendering parameters. Other machine-learnt model representations may be used, such as a hierarchy of matrices or other non-linear models.

The trained model is stored in a memory. Any memory may be used. The memory used for the training data may be used. For application, the memory may be in other devices. For example, the trained model is stored in a memory of a server. The server uses the trained model to output rendering parameters to clients or to a server-based renderer which outputs rendered images to the clients. As another example, multiple copies of the trained model are provided to different physicians, medical scanners, and/or workstations for use by different physicians.

Figure 2:
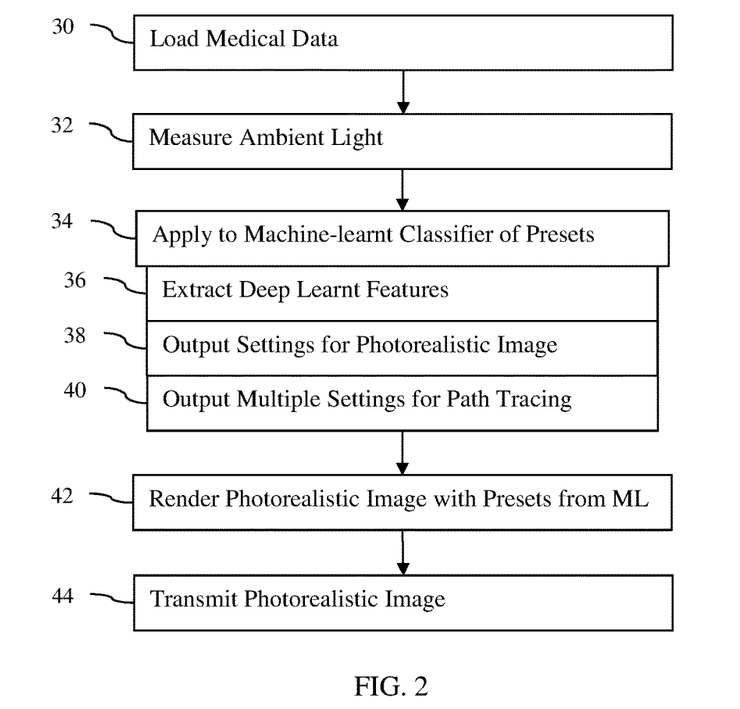
FIG. 2 is a flow chart diagram of an embodiment of a method for content-based rendering based on machine learning in a rendering system.

FIG. 2 shows one embodiment of a method for content-based rendering based on machine learning in a rendering system. The machine-learnt model or artificial intelligence agent is applied. For a given patient, a rendering of a scan dataset is to be performed. The artificial intelligence agent is applied to the scan dataset with or without other input information, outputting values for the rendering parameters. The values result in consistency in photorealistic rendering, possibly avoiding time consuming manual adjustment of various rendering parameters to achieve the desired visual.

The method is implemented by a computer, server, or other processor with a graphics processing unit or other renderer and a display. For example, medical data is loaded from memory. A light sensor measures the ambient light or captures a light probe image, and a computer applies the machine-learnt model, outputting values for rendering. A renderer uses the values to render from the medical data, resulting in transmission of the rendered image to a display. Different devices may be used, such as a controller or medical scanner processor performing the application and/or rendering.

Additional, different, or fewer acts may be provided. For example, the ambient light is not measured in act 32. As another example, the rendering of act 42 and transmission of the photorealistic image of act 44 are not provided, but instead the values of the rendering parameters are stored or transmitted. In yet another example, acts for manual adjustment and/or initial setting of one or more rendering parameters are provided, such as for an interactive rendering workflow. In other examples, none, one or two of acts 36-40 are performed without others of that set of acts.

The acts are performed in the order shown (top to bottom) or other orders. For example, the ambient light may be measured in act 32 prior to loading the medical data in act 30 and/or in parallel with performing act 34.

In act 30, medical data is loaded from a memory, sensors, and/or other source. A medical scanner may provide the data, such as a medical dataset representing a 3D region of the patient. Mining of a patient's computerized medical record may be used. Medical information from a picture archiving and communications server may be obtained. Any source may be used.

The medical data is for a given patient. While the training may use samples from many patients to learn features and/or learn to classify input medical data to provide values for rendering, the learnt model is applied to the medical data for a patient to output values for rendering parameters for that patient. The same or different machine-learnt models are applied to data for any number of patients.

Any type of medical data is obtained. Scan data representing a 3D volume is loaded as a medical dataset. The scan data may be from multiple two-dimensional scans or may be formatted from a 3D scan. The medical data may include non-image or non-scan data, such as patient test results, physician notes, lab results, diagnosis information, billing codes, clinical data, patient history, or other information.

The medical data includes the information learned to be used by the machine-trained model. Ground truth information and/or similarity or quality metric measures may be not provided. Where the machine learning learned to use feedback of predicted ground truth, then that feedback may be created and used as an input. The content to be used to determine the settings of the rendering parameters is provided to the machine-learnt model. For example, just the 3D scan data is provided as a medical dataset for a given patient. As another example, the 3D scan data and diagnostic information are provided as the medical dataset for the patient. The diagnostic information may be used to select the machine-learnt model to use and/or be part of the input feature vector.

Some machine-learnt models may be robust or still operate with some of the input feature vector missing. Alternatively, all of the information needed for the input feature vector is loaded.

In act 32, a sensor measures ambient light. Any luminosity sensor may be used, such as a charge coupled device. The sensor provides a measure of the luminosity. This measure may be used as an input in the input feature vector and/or to select a particular machine-learnt model to use. In alternative embodiments, the rendering is not based on ambient lighting conditions, so no measurement of ambient light is provided.

In an alternative embodiment for act 32, a light probe image is obtained as the measure of ambient light with a camera as the sensor. The image is obtained using any of a variety of ways and then used for high dynamic range image-based illumination during rendering. Examples ways for obtaining light probe images include capturing high-dynamic range photographs of a mirrored ball, stitching multiple photographs, or using self-contained panoramic cameras.

In act 34, the medical dataset is applied to the machine-learnt model. The loaded medical dataset is processed by a machine, such as a computer, processor, or server. The machine uses the internal representation of the machine-learnt model. The input feature vector is created and/or is the medical dataset. The machine inputs the feature vector, resulting in the machine-learnt model outputting the rendering settings based on the learned knowledge.

Acts 36-40 represent different acts in applying the machine-learnt model of presets for one or more rendering parameters. Additional, different, or fewer acts may be provided.

The machine-learned model was previously learned using any approach for machine learning, so may be a regression, classification, or reinforcement-learnt model. In one embodiment, the machine-learned model is trained with deep learning (e.g., deep neural network) to extract features from the medical dataset. By applying the deep-learnt model in act 36, features are extracted from the medical dataset. One or more other features may be extracted from the medical dataset using manually or user configured features. These features may then be used by another machine-learnt model and/or another hierarchal stage to output the values for the rendering. For example, a further reinforcement-learnt model is applied. The extracted features are input to the machine-learnt model for application.

Where the training was for consistency, the application of the machine-learnt model is more likely to output values in act 38 resulting in the photorealistic image corresponding to a standard image despite differences in the medical dataset. The photorealistic image is created using path tracing, other physically-based rendering, or reference photographs. The model uses the input feature vector to predict the values for rendering that result in the rendering of the scan data as an image with desired characteristics. The standard image may be a group of images having similar characteristics, such as resolution and/or contrast for a particular type of tissue or lesion. The rendering values output were learnt in order to provide the same or similar resolution and/or contrast for that particular type of tissue. Different machine-learnt models may be used for different diagnostic and/or workflow situations, such as outputting values for breast cancer imaging or for fetal imaging.

In another embodiment, the ambient light measured in act 32 is applied to the machine-learnt model with or as part of the medical dataset. The machine-learnt model is trained to output the values based in part on the ambient light. By applying the ambient light measure, the machine-learnt model outputs values for the rendering parameters that account for ambient light. Photorealistic images may be output as if lit by the ambient light in a room or to which the patient is subjected. Where the photorealistic images are used for augmented reality, use of ambient light and consistency in imaging accounting for ambient light may result in better blending or greater visual appeal.

The machine-learnt model is trained to output any number of values for a respective number of rendering parameters in act 40. For example, values for two or more physically-based rendering parameters are output based on the input medical dataset. Three or more, all, or a sub-set of any number of rendering parameters may have their values output by application to the machine-trained model or group of models. Example rendering parameters include controls for consistent data handling, transfer function, lighting design, viewing design, material propriety, or internal renderer parameters. One or more of the output values are for non-transfer function parameters.

In an example embodiment, the machine-learnt model or set of models output values for all of the rendering parameters except for viewing design. One or more parameters for viewing design are left to the user, such as for user navigation or setting of the camera position, orientation, and/or scale. The user inputs the values for all or some of the viewing design parameters, and the application of the medical dataset to the machine-learnt model provides the values for all of the other rendering parameters. Additional, different, or fewer types of rendering parameters may use initial input by the user.

The user may adjust model output values. Since physically-based rendering may be more time consuming than traditional rendering, providing a comprehensive set of values for the rendering parameters more likely to result in the desired image initially may avoid time-consuming adjustments. The user may, however, make any number of adjustments. The number and/or amount of change may be less due to the assistance by the machine-learnt model.

In act 42, a physically-based renderer renders the photorealistic image of the 3D region of the patient using the values output from the application. The output values of the machine-learnt model are used as settings by the physically-based renderer. For example, a sub-set or all of the rendering parameters for rendering with unbiased path tracing have values established by the output of the machine-learnt model.

The physically-based renderer is a graphics processing unit, array of graphics processing units, workstation, server, computer, or other machine capable of the required computations. Any physically-based rendering algorithm capable of computing the light transport may be used, such as path tracing, unbiased path tracing, Monte-Carlo path tracing, or Metropolis light transport. The physically-based rendering simulates the physics of light propagation to create an image instead of accumulating volume samples with local illumination along viewing rays from the camera, as is done for traditional volume rendering. In path tracing implemented for physically-based rendering, the paths of light or photons, including due to scattering and absorption, are modeled and used for rendering. The physically-based rendering result may be built up over time as the rendering may rely on probabilistic scattering and tracing millions of light paths.

The rendering results in a photorealistic image. A sequence of images may be provided as the image is built or rendered. Alternatively, for a given set of values of rendering parameters, a single image is output. In either case, the photorealistic image is rendered using presets from, at least in part, the machine-learnt model. A sequence of images due to alteration of values for one or more rendering parameters may be output. The user or renderer may change the values, such as rotation of a camera or for modeling fly-through.

In act 44, the renderer, host computer of the renderer, or other device transmits the photorealistic image or images. The transmission is over a bus, through a network interface, over a network, to a memory, or to a display. For example, the image is loaded into a buffer and output from the buffer to a display for viewing by a physician to aid diagnosis or pre-operative planning. A computer-generated representation of the medical data suitable for viewing by human users (e.g., 2D images, videos, stereoscopic image pairs, volumes, holograms, or lightfields) is output. Alternatively, the output may be for storage and/or for further machine analysis.

The transmission may be for any one or more of various purposes. In one embodiment, the transmission of the photorealistic image is part of a diagnostic report. A given diagnostic report may be specific to context, such as a report for kidney stones. Any kidney stones should be visible in an image. The photorealistic image shows kidney stones based on the values of the rendering parameters output by the model trained to create such images. The optimal context-specific images are provided for an automated diagnostic report in the clinical workflow.

In another embodiment, the transmission is to a display as an initial image for interactive viewing. The machine-learnt model is used to initialize interactive viewing applications in the clinical workflow. By providing values for rendering parameters so that the images are consistent with an established visualization design, the amount of user interaction may be reduced.

In yet another embodiment, the transmission is to an augmented reality device. For example, a physician may wear augmented reality glasses. The photorealistic image, with or without added annotations or graphics, is projected onto the glasses as an overlay on the actual view seen by the wearer. In other example, the photorealistic image is combined with a camera image and/or is used as a replacement for the camera image. In an augmented reality setup, the rendered image may be overlaid onto a live stream of real-time medical images (ultrasound, x-ray, optical laparoscopy, etc.).

Figure 3:
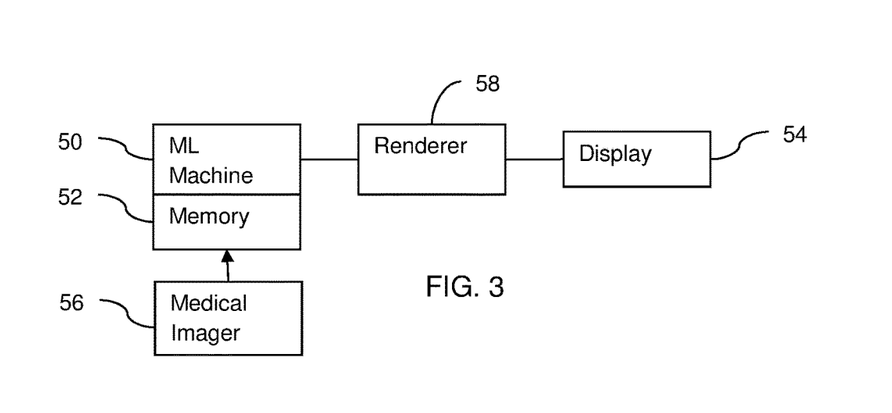
FIG. 3 is a block diagram of one embodiment of a system for content-based rendering based on machine learning.

FIG. 3 shows a block diagram of one embodiment of a system for content-based rendering based on machine learning. The system is for training with machine learning and/or application of a machine-learnt model. Using deep learning, learning to provide consistent images despite variability of input scan data, and/or learning a plurality of physically-based rendering parameters, a machine-learnt model is trained to output settings for rendering parameters given a new volume for a patient.

The system implements the method of FIGS. 1 and/or 2. Other methods or acts may be implemented, such as providing a user input (e.g., mouse, trackball, touch pad, and/or keyboard) and user interface for interactive rendering.

The system includes a machine 50, a memory 52, a display 54, a medical imager 56, and a renderer 58. Additional, different, or fewer components may be provided. For example, the medical imager 56 and/or memory 52 are not provided. In another example, a network or network connection is provided, such as for networking with a medical imaging network or data archival system. A user interface may be provided for interacting with the machine 50, renderer 58, or other components.

The machine 50, memory 52, renderer 58, and/or display 54 are part of the medical imager 56. Alternatively, the machine 50, memory 52, renderer 58, and/or display 54 are part of a server, workstation, or computer separate from the medical imager 56. The machine 50, memory 52, renderer 58, and/or display 54 are a personal computer, such as desktop or laptop, a workstation, a server, a network, or combinations thereof. In yet other embodiments, the machine 50 and memory 52 are part of a separate computer from the renderer 58.

The medical imager 56 is a medical diagnostic imaging system. Ultrasound, CT, x-ray, fluoroscopy, positron emission tomography (PET), single photon emission computed tomography (SPECT), and/or MR systems may be used. The medical imager 56 may include a transmitter and includes a detector for scanning or receiving data representative of the interior of the patient. The medical imager 56 acquires scan data representing the patient. The scan data may represent a volume of the patient. For example, scan data is acquired and used for diagnosis or surgical planning, such as identifying a lesion or treatment location.

In alternative embodiments, the medical imager 56 is not provided, but a previously acquired dataset for a patient is stored in the memory 52. In yet other alternatives, many medical images 56 are provided in the memory 52 as the training data, which is gathered and stored in the memory 52.

The machine 50 is a computer, workstation, server, processor, or other device configured to apply machine learning and/or to apply a machine-learnt model. The machine 50 is configured by software, hardware, and/or firmware. For learning, the machine 50 is configured by one or more machine learning algorithms. For applying a learnt model, the machine 50 is configured, in part, by a learnt matrix or matrices associating input data to output values.

The machine 50 applies a machine-learnt model, such as one learnt with deep learning. The machine-learnt model, as implemented by the machine 50, generates input features and/or outputs settings for rendering parameters based on application of medical data from a scan of a patient. The rendering parameters include windowing, transfer function, lighting, and/or material properties. The settings are learnt to provide an image similar in look and/or feel to one or more images from a same diagnostic context. Consistent images, such as to highlight or show anatomy of interest, are created. The diagnostic context provides the standard or information of interest.

The memory 52 is a graphics processing memory, a video random access memory, a random access memory, system memory, cache memory, hard drive, optical media, magnetic media, flash drive, buffer, database, combinations thereof, or other now known or later developed memory device for storing training data, rendering parameters values, medical datasets, and/or other information. The memory 52 is part of the medical imager 56, part of a computer associated with the machine 50, part of a computer associated with the renderer 58, a database, part of another system, a picture archival memory, or a standalone device.

The memory 52 stores scan data representing one or more patients. For example, data from the medical imager 56 is stored. The data is in a scan format or reconstructed to a volume or three-dimensional grid format. The scan data is stored for training and/or stored for rendering an image of a patient.

The memory 52 or other memory is alternatively or additionally a non-transitory computer readable storage medium storing data representing instructions executable by the programmed machine 50 for learning or applying the machine-learnt model. The instructions for implementing the processes, methods, and/or techniques discussed herein are provided on non-transitory computer-readable storage media or memories, such as a cache, buffer, RAM, removable media, hard drive, or other computer readable storage media. Non-transitory computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The renderer 58 is a graphics processing unit, graphics card, graphic chip, multi-core processor, or other processor for running a software package that implements the photorealistic image generation functionality. The renderer 58 is configured by an application programming interface to render an image from the 3D scan data representing a patient. Using physically-based rendering, a photorealistic image is rendered. Using the settings output by the machine-learnt model, path tracing is applied to render the image. For feedback in training, the renderer 58 may render training images. Similarity is calculated by the renderer 58 and/or the machine 50.

The display 54 is a monitor, LCD, projector, plasma display, CRT, printer, or other now known or later developed device for displaying the photorealistic image or images. The display 54 receives images from the machine 50, memory 52, renderer 58, or medical imager 56. The images of the tissue captured by the medical imager 56 are displayed. Other information may be displayed as well, such as generated graphics, text, or quantities as a virtual overlay.

Additional images may be displayed. Where scan data represents a sequence of scans over time, a corresponding sequence of images may be generated. For interactive rendering, new images may be generated as settings for one or more rendering parameters are changed by a user.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for content-based rendering based on machine learning in a rendering system, the method comprising:
    loading, from memory, a medical dataset representing a three-dimensional region of a patient;
    applying, by a machine, the medical dataset to a machine-learnt model, the machine-learned model trained with deep learning to extract features from the medical dataset and trained to output values for two or more volume rendering parameters that correspond to input of the medical dataset, the two or more volume rendering parameters being settings of a volume renderer, the settings used by the volume renderer to control rendering, from three dimensions to two-dimensions, an image of the three-dimensional region of the patient;
    rendering, by the volume renderer, the image of the three-dimensional region of the patient from the medical dataset using the output values resulting from the applying as the settings to control the rendering from the medical dataset, the rendering of the medical dataset of the three-dimensional region being to the image in the two-dimensions; and
    transmitting the image.

2. The method of claim 1 further comprising loading patient information other than the medical dataset representing the three-dimensional region of the patient.

3. The method of claim 1 wherein applying comprises applying to output the values for the two or more volume rendering parameters as all of controls for data consistency handling, lighting design, material propriety, and internal renderer property based on applying user input of viewing design and the medical dataset.

4. The method of claim 1 wherein applying comprises applying with the machine-learnt model trained to output the values resulting in the image corresponding to a standard image despite differences in the medical dataset.

5. The method of claim 1 wherein applying comprises applying with the machine-learnt model comprising a regression, classification, or reinforcement learnt model.

6. The method of claim 1 wherein applying comprises applying with the deep learning as a deep neural network.

7. The method of claim 1 wherein applying comprises applying with the machine-learnt model as a deep reinforcement learnt model.

8. The method of claim 1 wherein rendering comprises rendering with unbiased path tracing.

9. The method of claim 1 wherein transmitting comprises transmitting as part of a diagnostic report, as an initial image of an interactive viewing, or as an overlay in augmented reality.

10. The method of claim 1 further comprising:
    measuring ambient light with a light sensor;
    wherein applying comprises applying the ambient light and the medical dataset, the machine-learnt model trained to output the values based in part on the ambient light.

11. A method for machine training for content-based rendering in a machine training system, the method comprising:
    inputting first volume data of a volume of a patient, a first image of the volume, and first values of rendering parameters to training of an artificial intelligence, rendering parameters being settings to control rendering from the volume to a two-dimensional image;
    machine training, with a machine, the artificial intelligence to output second values of the rendering parameters for second volume data where the second values control the rendering from the volume to provide a second rendered image of the second volume data modeled on the first image; and
    storing the trained artificial intelligence.

12. The method of claim 11 wherein inputting comprises inputting the patient non-image information to the training.

13. The method of claim 11 wherein training comprises training the artificial intelligence to output the second values as two or more of data consistency, transfer function, lighting, and viewing parameters.

14. The method of claim 11 wherein training comprises training the artificial intelligence to output the second values based on user selected viewing camera parameters, the rendering parameters for which second values are to be output being other than the viewing camera parameters.

15. The method of claim 11 wherein training so the second rendered image is modeled after the first rendered image comprises training with a metric of similarity between the first rendered image and the second rendered image.

16. The method of claim 11 wherein the first image comprises a reference photograph or video of the patient.

17. The method of claim 11 wherein inputting comprises perturbing the rendering parameters, creating a collection of sets of the rendering parameters, and wherein training comprises training based on selection of a sub-set of the sets.

18. The method of claim 17 wherein selection of the sub-set comprises selection by a user based on visual examination of images rendered using the sets.

19. The method of claim 11 wherein machine training comprises deep learning with regression, classification, or reinforcement learning.

20. The method of claim 19 wherein machine training comprises deep reinforcement learning with a similarity of the second rendered image to the first image as a reinforcement.

21. The method of claim 20 wherein deep reinforcement learning comprises selecting with a probability distribution of different similarities including the similarity.

22. A system for content-based rendering based on machine learning, the system comprising:
   a medical scanner configured to scan a patient;
   a machine configured to output settings for rendering parameters by application of data from the scan to a machine-learnt model, the rendering parameters being controls for performing rendering from a volume to a two-dimensional image, and the settings learned to provide a first image from the data similar to one or more second images for a same diagnostic context; and
   a graphics processing unit configured to render the first image from the data using the settings output by the application of the data to the machine-learnt model, the first image being a two-dimensional representation.

23. The system of claim 22 wherein the machine-learnt model is machine learnt with deep learning.

24. The system of claim 22 wherein the rendering parameters comprise material properties, viewing properties, lighting properties, windowing properties, and internal renderer properties, and wherein the graphics processing unit is configured to render with path tracing using the settings.

* * * * *